US 8,481,277 B2
Jul. 9, 2013

(12) United States Patent
Ladenson et al.

(54) ALZHEIMER'S DIAGNOSIS

(75) Inventors: Jack H. Ladenson, St. Louis, MO (US); Omar Laterza, New York, NY (US); Vijay Modur, Acton, MA (US)

(73) Assignee: Washington University, St. Louis, MO (US)

( * ) Notice: Subject to any disclaimer, the term of this patent is extended or adjusted under 35 U.S.C. 154(b) by 154 days.

(21) Appl. No.: 12/674,153

(22) PCT Filed: Aug. 21, 2008

(86) PCT No.: PCT/US2008/073851
§ 371 (c)(1),
(2), (4) Date: Feb. 24, 2011

(87) PCT Pub. No.: WO2009/026432
PCT Pub. Date: Feb. 26, 2009

(65) Prior Publication Data
US 2011/0136254 A1    Jun. 9, 2011

Related U.S. Application Data

(60) Provisional application No. 60/957,132, filed on Aug. 21, 2007.

(51) Int. Cl.
*G01N 33/53* (2006.01)
*G01N 33/567* (2006.01)
*G01N 33/566* (2006.01)

(52) U.S. Cl.
USPC ......... 435/7.92; 435/7.1; 435/7.21; 435/7.8; 435/7.9; 436/501; 436/503

(58) Field of Classification Search
None
See application file for complete search history.

(56) References Cited

U.S. PATENT DOCUMENTS

| 5,837,672 A * | 11/1998 | Schenk et al. ............... 514/17.8 |
| 2002/0025527 A1 | 2/2002 | Crawford et al. |
| 2005/0244890 A1 | 11/2005 | Davies et al. |

FOREIGN PATENT DOCUMENTS

| WO | WO-2004/007675 | 1/2004 |
| WO | WO-2006/012351 | 2/2006 |
| WO | WO-2006/012354 | 2/2006 |

OTHER PUBLICATIONS

Braunewell et al., Dement Geriatr Cogn Disord, 2001,12:110-6.*
Andreasen et al., World J Biol Psychiatry, 2003, 4:147-55.*
International Search Report for PCT/US08/73851, mailed on Nov. 13, 2008, 1 page.
International Preliminary Report on Patentability for PCT/US08/73851, issued Feb. 24, 2010, 6 pages.
Formichi et al., Journal of Cellular Physiology (2006) 208(1):39-46.
Lee et al., Clinical Chemistry (2008) 54(10):1617-1623.
Schnurra et al., Neurobiology of Disease (2001) 8(5):900-909.
Schoonenboom et al., Neurology (2004) 62:1580-1584.
Supplementary European Search Report for EP 08827578.9, mailed Aug. 5, 2010, 10 pages.

* cited by examiner

*Primary Examiner* — Olga N Chernyshev
(74) *Attorney, Agent, or Firm* — Morrison & Foerster LLP

(57) ABSTRACT

Evaluation of VLP-I levels in combination with at least one of amyloid-β peptide (AB), hyperphosphorylated tau (pTau) or total tau (tTau) levels in samples of biological fluid improves the accuracy of diagnosis of Alzheimer's disease.

6 Claims, 4 Drawing Sheets

ALZHEIMER'S DIAGNOSIS

CROSS-REFERENCE TO RELATED APPLICATIONS

This application is the national phase of PCT application PCT/US2008/073851 having an international filing date of 21 Aug. 2008, which claims priority to U.S. Provisional Application Ser. No. 60/957,132 filed 21 Aug. 2007. The contents of these documents are incorporated herein by reference.

TECHNICAL FIELD

The invention relates to a method and kits to diagnose neurodegenerative disease such as Alzheimer's disease. More specifically, it concerns the methods used to diagnose disease using biomarkers.

BACKGROUND ART

The diagnosis of Alzheimer's disease (AD), the most common form of dementia in Western countries, is largely based on historical and clinical criteria. Although many studies report a reasonably high degree of diagnostic accuracy (80-90%), often these studies include patients evaluated at specialized centers with advanced disease. At present, post-mortem examination of brain tissue is the only tool for definitive diagnosis. Therefore, the development of a biomarker for AD would aid greatly in the diagnosis of this disease. In addition, such a marker could potentially be utilized to measure efficacy in future therapeutic trials.

Most studies of AD biomarkers to date have focused on known pathological substrates for the disease. Pathological hallmarks of AD include amyloid plaques and neurofibrillary tangles, both comprised primarily of abnormally aggregated endogenous proteins. Amyloid plaques are extracellular proteinaceous aggregates. They are principally composed of the amyloid-β peptide (Aβ), a 38-42 amino acid peptide fragment of the amyloid precursor protein (APP). The major species, a 42-amino acid peptide (Aβ1-42), is significantly decreased in the cerebrospinal fluid (CSF) of patients with AD. Neurofibrillary tangles are intraneuronal protein aggregates found mainly in neuritis. The neurofibrillary tangles are primarily composed of hyperphosphorylated Tau (pTau), a microtubule-associated protein. Several studies have shown that total Tau (tTau) and pTau are elevated in AD CSF.

Although studies exploring the use of these two biomarkers in the diagnosis of disease have been carried out, the results have not led to a useful, definitive method. Significant overlap in values for these biomarkers between cases and controls limits their utility as diagnostic biomarkers. In addition, several reports have demonstrated the lack of correlation between amyloid plaque load and the degree of dementia, suggesting that the former may not directly relate to the latter. At present, there is a need for an improved tool more reliable than those currently available for the diagnosis of Alzheimer's disease.

Another class of biomarkers that may have utility in the diagnosis of AD, are biomarkers that reflect neuronal death rather than specific markers of disease pathogenesis. Such markers may provide information about disease progression related to functional outcome, and have utility in future clinical trials testing therapeutic efficacy.

An example of such a biomarker is Visinin-like protein 1 (VLP-1), a calcium sensor protein which is expressed in high abundance in neurons of the central nervous system. VLP-1 is elevated in the CSF of rats following transient focal ischemia, and is detectable in elevated concentrations in the plasma of ischemic stroke patients. The use of VLP-1 as a marker for brain damage and for AD has been described in PCT publication WO 2006/012351. Thus, while VLP-1 indicates brain damage, it has also been identified as a useful diagnostic for Alzheimer's disease. Alternative causes for brain damage are associated with readily identified conditions such as stroke, asphyxiation, invasive surgery and trauma.

DISCLOSURE OF THE INVENTION

The invention provides methods that include the VLP-1 biomarker to predict the imminence and progression of Alzheimer's disease. When an elevated level of VLP-1 is detected in bodily fluids, e.g., in cerebrospinal fluid or in serum, it is associated with brain injury such as that caused by Alzheimer's disease (AD).

Thus, the invention is directed to a method to diagnose AD which method comprises evaluating VLP-1 in combination with at least one other biomarker selected from amyloid-β peptide (Aβ), hyperphosphorylated Tau (pTau) and total Tau (tTau). Evaluating VLP-1 in combination with another biomarker gives rise to an improved diagnostic method better than that of relying on the interpretation of any one biomarker alone. Evaluating VLP-1 in combination with copy presence of a ApoE ε4 allele also improves the diagnostic method.

Also included within the scope of the invention are kits for diagnosis which contain reagents for quantifying the biomarker targets including VLP-1 and at least one of Aβ, pTau, tTau present in the biological fluid samples, as well as kits that contain reagents for quantifying VLP-1 and assessing the presence or absence of the ApoE2 ε4 allele.

BRIEF DESCRIPTION OF THE DRAWINGS

FIG. 2A shows the area under ROC curve (AuC) and its 95% confidence interval for VLP-1, Aβ, pTau and an optimum linear combination of all 3 biomarkers (ALL). FIG. 2B shows CSF levels of VLP-1, Aβ, and pTau plotted on a 3-D graph (controls, solid circles; AD, open circles).

FIG. 4A shows CSF VLP-1 levels plotted against Aβ. FIG. 4B shows CSF VLP-1 levels plotted against tTau. FIG. 4C shows CSF VLP-1 levels plotted against pTau. Correlation was most striking between VLP-1 and pTau (r2=0.73) compared to the others.

MODES OF CARRYING OUT THE INVENTION

Figure 1:
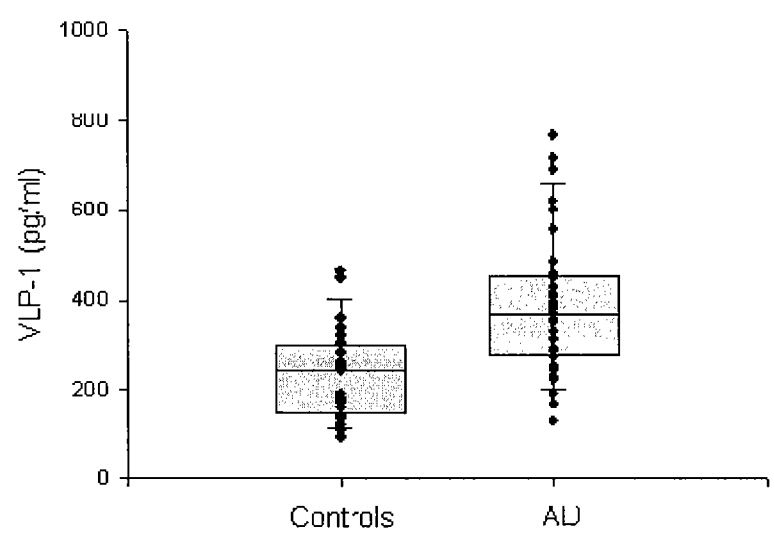
FIG. 1 shows CSF VLP-1 levels in AD patients and controls. The line within the box represents the median value; the box encompasses 25th-75th percentiles; and the error bars encompass the 10th-90th percentiles. A significant difference was found in control vs. AD patients; p<0.001, Student's T-test.

As described in the above-cited PCT publication WO 2006/012351, VLP-1 levels in biological fluids, especially cerebrospinal fluid correlate with the incidence of brain damage associated with Alzheimer's disease. It has now been found that by combining the results of determining VLP-1 levels with at least one alternative marker, selected from amyloid β peptide, hyperphosphorylated Tau, and total Tau, the accuracy of diagnosis can be improved. The accuracy can also be improved by correlation of VLP-1 levels with an ApoE ϵ4 genotype.

Methods for evaluating the levels of each of these markers are known in the art. Literature references which describe such methods are set forth in the examples below. However, the method of the invention is not limited to employing these precise methods; any method for determining these markers or for assessing the presence of an ApoE ϵ4 allele may be used. Such methods include immunoassays, chromatographic assays and the like.

The levels in a patient to be diagnosed are determined and compared with levels in normal controls. Typically, a standard value for normals with appropriate error bars can be generated by averaging the results from a statistically meaningful sample of individuals known not to be afflicted by this condition. As noted herein, typically, in CSF, levels of VLP-1, tTau and pTau are significantly higher in AD patients and levels of Aβ1-42 are lower. As noted in the examples below, the average values for controls with appropriate error bars are shown in Table 2.

The levels of the relevant markers in normal controls may be determined experimentally in the course of performing the method of the invention with respect to a test subject on a statistically meaningful number of subjects, typically 10 or more subjects, 20 or more subjects, 30 or more subjects or 50 or more subjects. However, values associated with levels of these markers in normal controls may also be published in the literature; in such instances it is unnecessary to determine the levels of a published marker in normal controls, but rather these values can be obtained by consulting the literature. The practitioner will understand when, and whether, published values for the level of a particular marker is sufficiently reliable, and has been determined by methods sufficiently similar to that used in performing the test on test subjects to be satisfactory for making the comparison.

The kits designed for conducting the method of the invention will contain reagents for the determination of VLP-1 plus the reagents for determination of at least one additional marker or for determining the presence of an ApoE ϵ4 allele. The nature of the reagents will depend on the type of methodology used in performing the test. If immunological assays such as radioimmunoassays, ELISA's, or Western blot are to be employed, antibodies reactive with the marker, such as VLP-1, will be included. Such antibodies may be polyclonal or monoclonal or recombinantly produced. As the assays are performed in vitro, humanized forms are unnecessary, but are not excluded from use in the practice of the invention. Generally, these are less preferred in this context, however, as the affinity tends to be lower.

Typically, also, the kits will contain instructions for conducting the determinations of marker levels, and may further contain directions for statistical comparisons between levels in test subjects and those in normal controls.

The test subjects are typically those persons identified as at risk for Alzheimer's disease but may also include individuals who are lacking in any symptoms that would lead to a suspicion of susceptibility. The subjects may have already been shown to have elevated levels of one of the markers employed in the method of the invention, in which case the result of the previous test in combination with the test for at least one additional marker constitute the data provided for conduct of the method of the invention. Thus, the invention further includes a method of simply assessing the results of previous determinations of one or more markers in combination with an level of VLP-1 and need not include physically determining the levels of these previously measured markers. The methods of the invention also include simply comparing the levels of VLP-1 and at least one additional marker selected from amyloid-β peptide, hyperphosphorylated Tau, and total Tau that have previously been determined in a test subject with levels previously determined in control subjects and determining whether the levels of both markers are different in the test subject in the predicted way in order to determine the presence of absence of Alzheimer's disease in the test subject.

Biological fluids that are possible sample sources include blood and fractions thereof, such as plasma or serum, cerebrospinal fluid, urine, and lymphatic fluids. Serum or plasma or urine are more convenient. Cerebrospinal fluid is the preferred source for sampling.

The following examples are intended to illustrate but not to limit the invention.

Example 1

Evaluation of Patients

Thirty-three (33) patients with a clinical diagnosis of AD (NINCDS-ADRDA criteria for probable AD) were evaluated. Twenty-four (24) healthy controls also participated and were free of neurological or psychiatric disorders. All subjects underwent a clinical evaluation which included a medical history, physical and neuropsychiatric evaluation, and a Mini-Mental State Examination (MMSE). ApoE genotype was also assessed. See Table 1.

TABLE 1

Demographics of Study Subjects

|  | N | Age | Female | Duration | apoE4 | MMSE |
|---|---|---|---|---|---|---|
| Controls | 24 | 68.5 ± 1.3 | 11 (46%) | N/A | ND | 29.8 ± 0.1 |
| AD | 33 | 64.9 ± 2.5 | 18 (55%) | 3.9 ± 0.4 | 25 | 23.0 ± 1.1 |
| p value |  | 0.248 |  |  |  | <0.001 |

The mean age of subjects in each group did not differ significantly (controls: 68.5 years vs. AD 64.9 years). Gender distribution was also not significantly different (46% vs. 55%). The mean duration of disease in the AD group was 3.9 years. MMSE scores were assessed and were significantly lower in the AD group (23.0 vs. 29.8, p<0.001).

Example 2

Determination of tTau, pTau, Aβ1-42, and VLP-1 Levels in CSF

CSF samples were collected by lumbar puncture at the L3/L4 interspace. The first portion of the sample was discarded, and the subsequent 10 mls was collected in polypropylene tubes, centrifuged at 2,000 g for 10 min (to eliminate cells), and frozen in aliquots at −80° C. All samples had less than 500 erythrocytes/4

CSF samples were assayed for total Tau (tTau) and hyperphosphorylated Tau (pTau at Thr-181), and Aβ1-42 using sandwich ELISA's, as previously described (Blennow, K., et al., *Mol. Chem. Neuropathol.* (1995) 26:231-245; Vanmechelen, E., et al., *Neurosci. Lett.* (2000) 285:49-52). CSF VLP-1 was measured using a sandwich ELISA (monoclonal antibody for capture and rabbit polyclonal antibody for detection), as described (Laterza, O. F., et al., *Clin. Chem.* (2006) 52:1713-1721).

The CSF tTau and pTau levels were significantly higher in AD patients compared to controls (p<0.001 for both, Table 2) consistent with earlier findings (Arai, H., et al., *Ann. Neurol.* (1995) 38:649-652; Blennow, et al., supra; Tapiola, T., et al., *Neuroreport* (1997) 8:3961-3963; Andreasen, N., et al., *World J. Biol. Psychiatry* (2003) 4:147-155). $A\beta_{1-42}$ levels were lower in AD patients compared to controls (p<0.001, Table 2), consistent with numerous other studies (Arai, et al., supra; Blennow, et al., supra; Tapiola, et al., supra; Andreasen, et al., supra). The units in Table 2 are pg/mL of CSF.

TABLE 2

CSF Levels in Controls and AD Patients

|  | tTau | pTau | $A\beta_{1-42}$ | VLP-1 |
|---|---|---|---|---|
| Controls | 395 ± 42 | 61 ± 6 | 698 ± 47 | 234 ± 21 |
| AD | 735 ± 77 | 100 ± 7 | 471 ± 30 | 387 ± 27 |
| p value | <0.001 | <0.001 | <0.001 | <0.001 |

VLP-1 levels in the CSF were significantly higher in the AD patients compared to controls (387±27 vs. 234±21, p<0.001, FIG. 1).

Example 3

Statistical Analysis of the Biomarkers

Differences in patient characteristics and biomarkers between two groups were compared using chi-square test or student's t-test as appropriate. ANOVA with a post-hoc Tukey's test was used for comparisons between multiple groups. The diagnostic ability of these biomarkers was evaluated using receiver operating characteristic (ROC) curves which plot true positive rates (sensitivity) versus the false positive rates (1-specificity) across all possible thresholds. As a global measure for the accuracy of diagnosis, the area under ROC curve (AUC) was also calculated for each individual biomarker as well as for an optimum linear combination of all biomarkers (Xiong, C., et al., *Med. Decis. Making* (2004) 24:659-669). All the statistical comparisons were implemented using the statistical package SAS (version 9) while all ROC analyses were performed with ROCKIT, a widely used freeware available from the Kurt Rossmann Laboratories at the University of Chicago. A p value under 0.05 was taken to indicate significance and all statistical tests were two-sided.

Figure 2:
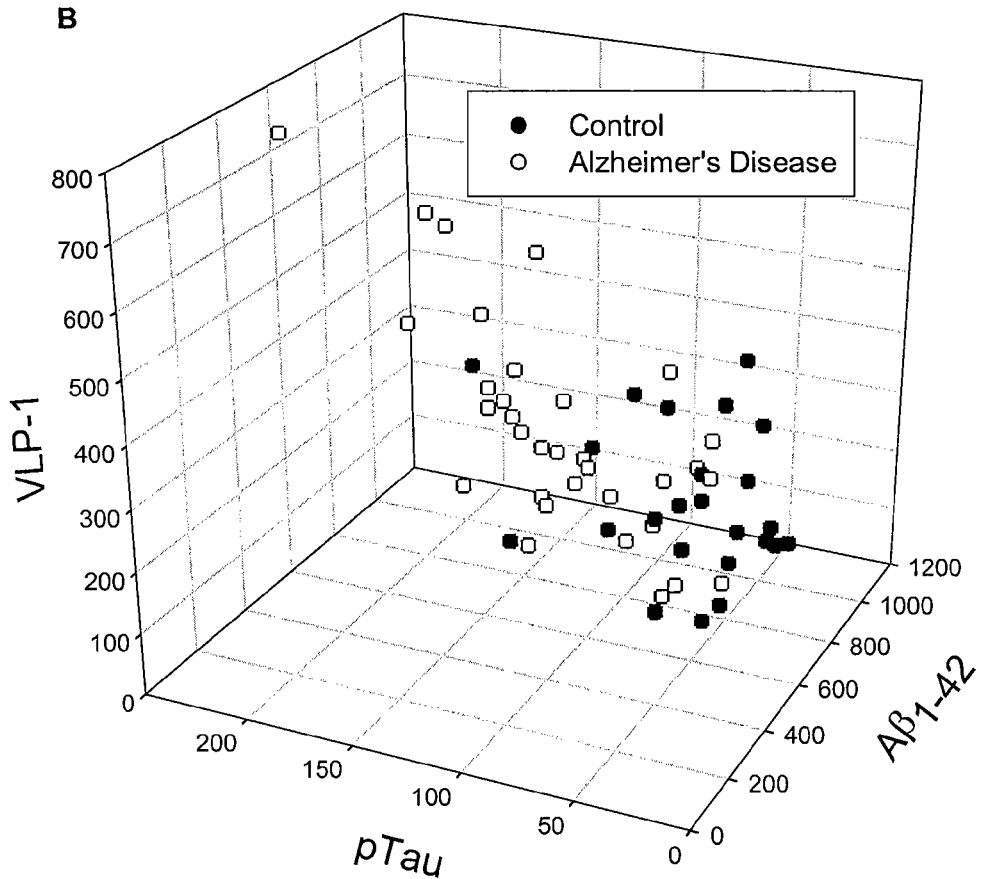
FIGS. 2A and 2B show the predictive ability of AD biomarkers to diagnose AD vs. Control.

We performed a receiver operating characteristic (ROC) analysis for each individual biomarker alone compared to the combination of all biomarkers. The area under the ROC curves for VLP-1, Aβ, pTau, and an optimum linear combination of all biomarkers is shown in FIG. 2A. The linear combination resulted in an approximately 5% improvement in diagnostic accuracy. The 3-D plot (FIG. 2B) demonstrates that higher levels of VLP-1 and pTau, and lower levels of Aβ1-42 result in AD diagnosis.

Example 4

Assessment of ApoE Genotype and VLP-1 Levels

Figure 3:
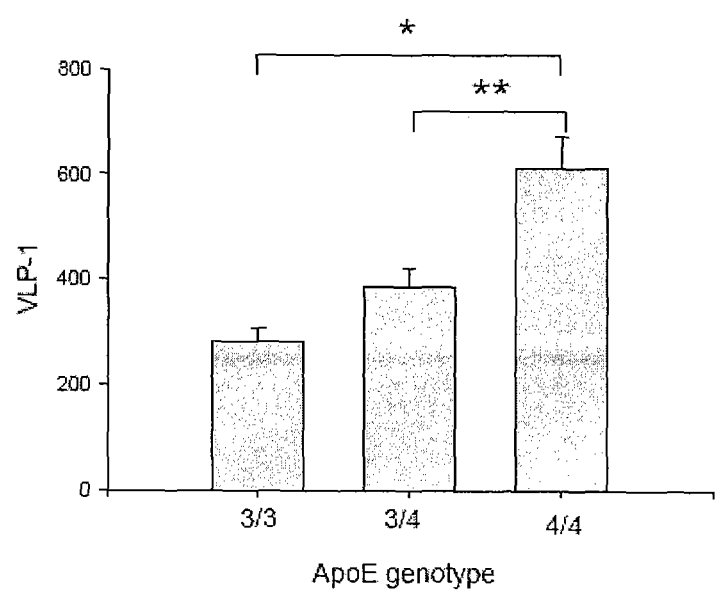
FIG. 3 shows VLP-1 levels by ApoE genotype. Mean CSF VLP-1 levels are graphed according to ApoE genotypes (ε3/ε3, ε3/ε4). Mean VLP-1 levels in ApoE ε4/ε4 were more than twice that in ε3/ε3 individuals; * p<0.0 (3/3 vs. 4/4); ** p<0.0 (3/4 vs. 4/4); using ANOVA with post-hoc Tukey's test.

Mean CSF VLP-1 levels were correlated by different ApoE genotypes within the cohort of AD patients. ApoE ε4/ε4 individuals (n=5) had the highest levels of VLP-1, followed by ε3/ε4 (n=20) and ε3/ε3 (n=8) individuals (FIG. 3). The ApoE ε4 genotype may be associated with increased neuronal death.

Example 5

Correlation of VLP-1 to Other Pathological Biomarkers

Figure 4:
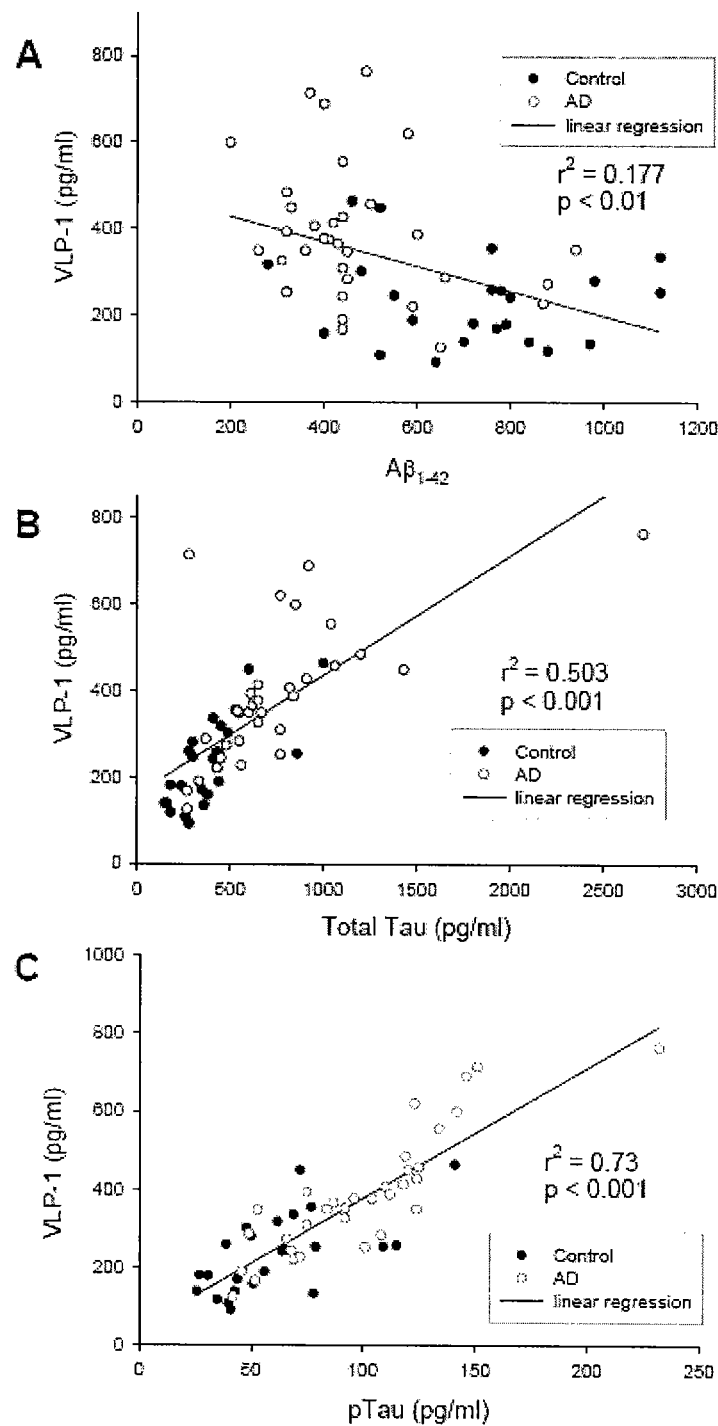
FIGS. 4A-4C show correlation of VLP-1 and pTau levels in CSF.

Correlations between VLP-1 and tTau, pTau, or Aβ1-42 were performed; VLP-1 and shown in FIGS. 4A-4C. pTau showed the greatest correlation (FIG. 4C, r2=0.73).

The invention claimed is:

1. A method of diagnosing Alzheimer's disease in a subject, which method comprises determining the level of Visinin-like protein 1 (VLP-1) in a sample of biological fluid of a human subject in combination with determining the level of at least one additional marker selected from amyloid-β peptide Aβ1-42, hyperphosphorylated Tau (pTau) and total Tau (tTau);

comparing the level of said markers with the levels of the same markers in normal controls, wherein a higher level of VLP-1 in combination with either a lower level of Aβ1-42 or higher level of pTau or higher level of tTau in said subject as compared to normal controls results in a diagnosis for said subject of Alzheimer's disease, and wherein said method provides an improvement in diagnostic accuracy of Alzheimer's disease diagnosis as compared to determinations based on VLP-1 or any of said additional biomarkers alone; and wherein the sample is obtained from cerebrospinal fluid, plasma or serum.

2. The method of claim 1, wherein the levels of at least two of said additional markers are determined and compared.

3. The method of claim 2, wherein the levels of all three of said additional markers are determined and compared.

4. The method of claim 1, wherein the levels of the markers in normal controls are determined experimentally in at least 20 normal human subjects.

5. The method of claim 1, wherein the levels of said markers in normal controls are obtained as literature values.

6. The method of claim 1, wherein said additional marker is Aβ1-42.

* * * * *

UNITED STATES PATENT AND TRADEMARK OFFICE
CERTIFICATE OF CORRECTION

PATENT NO. : 8,481,277 B2  Page 1 of 1
APPLICATION NO. : 12/674153
DATED : July 9, 2013
INVENTOR(S) : Ladenson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this
Eighth Day of September, 2015

Michelle K. Lee
*Director of the United States Patent and Trademark Office*